United States Patent [19]

Finkelman

[11] Patent Number: 4,689,400

[45] Date of Patent: Aug. 25, 1987

[54] ENHANCEMENT OF SPECIFIC ANTIBODY PRODUCTION WITH ANTI-IGD ANTIBODIES

[75] Inventor: Fred D. Finkelman, Rockville, Md.

[73] Assignee: The United States of America as represented by the Secretary of the Navy, Washington, D.C.

[21] Appl. No.: 749,681

[22] Filed: Jun. 27, 1985

[51] Int. Cl.$^4$ .......................... C07K 15/00; C07K 3/08
[52] U.S. Cl. ...................................... 530/389; 530/387; 530/390; 530/391; 424/85; 436/547; 436/507; 436/513; 435/68
[58] Field of Search .................. 424/85; 436/547, 513, 436/507; 530/387, 384–391; 435/68

[56] References Cited

U.S. PATENT DOCUMENTS

| | | |
|---|---|---|
| 3,410,839 | 11/1968 | Carvalho . |
| 4,178,359 | 12/1979 | Mondaubaugh et al. . |
| 4,236,893 | 12/1980 | Rice . |
| 4,273,756 | 6/1981 | Ling et al. . |
| 4,292,403 | 9/1981 | Duermeyer . |
| 4,427,653 | 1/1984 | Springer .............................. 424/88 |
| 4,478,823 | 10/1984 | Sanderson ........................... 424/88 |
| 4,493,793 | 1/1985 | Chu ...................................... 424/88 |
| 4,536,479 | 8/1985 | Vander-Mallie ...................... 424/88 |

FOREIGN PATENT DOCUMENTS

8504422 10/1985 PCT Int'l Appl. .................. 435/68
8601222 2/1986 PCT Int'l Appl. .................. 435/68

OTHER PUBLICATIONS

Finkelman et al., *J. Immunol*, 129(2), 1982, pp. 638–646.
Ryon et al., *J Immunol*, 130(6), 1983, pp. 2534–2541.
Forstrom et al., *Nature*, 303, 1983, pp. 627–629.
Primi et al., *J. Immunol*, 129(3), 1982, pp. 1124–1129.
Rose et al., *J. Immunol*, 128(5), 1982, pp. 2126–2133.
Marx, *Science*, 228, 1985, pp. 162–165.
Tahenori et al., *Eur J. Immunol*, 1982, 12, pp. 104–146.
Hunter et al., *Appl. Env. Microbical*, 1985, vol. 49.
Goldman et al., "Deposition of Idiotype–Anti-Idiotype ... after polycolonal B cell Activation", *J Exp Med*, 155, 1982, pp. 1385–1399.
"Preparation and Characterization of Monoclonal Antibodies to the Trichothecene Mycotoxin T-2", Applied & Environmental Microbiology, Jan. 85, pp. 168–172, Hunter, et al.

*Primary Examiner*—John Kight
*Assistant Examiner*—Garnette D. Droper
*Attorney, Agent, or Firm*—John L. Forrest; Wendell R. Guffey

[57] ABSTRACT

A method is disclosed for the production of antibodies to haptens which comprises binding the hapten to an antibody from one species, injecting the antibody-hapten into another species, and isolating the antibodies produced in response to the hapten.

16 Claims, No Drawings

4,689,400

ENHANCEMENT OF SPECIFIC ANTIBODY PRODUCTION WITH ANTI-IGD ANTIBODIES

BACKGROUND OF THE INVENTION

This invention pertains to a method for the production of antibodies and, in particular, to a simple and fast method for producing large quantities of IgG antibodies to specific antigens.

Generally, the term "antibody" refers to a protein that appears in the serum and certain cells of a vertebrate in response to the introduction of a protein or some other macromolecule foreign to that vertebrate species. This foreign molecule which stimulates antibody production specific for that molecule is called an "antigen". The specific antibody molecules generated to an antigen can combine with that antigen to form an antigen-antibody complex which destroys or alters the properties of that antigen. The production of antibodies and the binding of the antibodies to antigen molecules is one mechanism used by the body to fight disease-causing agents that have antigenic properties and to neutralize foreign toxic substances. This process is called the humoral immune response.

Antibodies produced in the immune response are divided into five classes that are designated IgG, IgA, IgD, IgE, and IgM. These classes are structurally related and each contains two heavy (H) chains and two light (L) chains, which are connected mainly by disulphide bridges and/or hydrogen bonds. Each class performs a distinct function in the immune response. For example, IgM antibodies are present in larger concentrations in the early stages of an infection, IgG antibodies are long-lasting in serum and promote the phagocytosis of microbes to which they have bound, IgA antibodies are the most abundant antibodies in gut and respiratory secretions, IgE antibodies promote allergic responses and the elimination of helminthic parasites, and IgD antibodies, which are abundant on the cell membranes of lymphocytes but scarce in serum, have a major role in the control of humoral immune responses.

For many antigens the production of antibodies can be initiated simply by injecting the antigens into an immunocompetent vertebrate. Such antigens stimulate the production of antibodies at serum concentrations sufficient to destroy the antigen and retain the "immunity" to that antigen for long periods. These antigens are called "strong antigens". In contrast, some antigens, perhaps because of their size or chemical composition, do not stimulate the production of antibodies when injected by themselves into a vertebrate. The vertebrate cannot, therefore, generate an immune response to such antigens under these circumstances. Immune responses to such "weak antigens" can be generated, however, if they are injected in combination with an adjuvant, such as mineral oil, killed tuberculus bacilli, Al(OH)$_3$, or killed *B. pertussis* bacilli.

A third class of compounds, the "haptens", fail to generate specific antibody production even when injected into animals along with an adjuvant. Haptens often can, however, generate strong antibody responses if they are physically bound to an antigenic carrier molecule and the hapten-carrier complex is injected into an animal. In general, the more strongly antigenic the carrier to which the hapten is bound, the greater will be the anti-hapten antibody response.

When it is not possible or practical to induce an immune response to an antigen or hapten in an animal by injecting the antigen by itself, with an adjuvant, or bound to an immunogenic carrier, it may still be possible to confer upon that animal the protective effects of the appropriate antibody. This may be acomplished by "passive immunization", a process in which a second animal, often of a different species, is stimulated to produce antibodies to the antigen in question, and serum or purified serum antibodies from the second animal is injected into the first. This process effectively transfers the "immunity" to the recipient animal.

However, neither of these techniques have been effective for some weak antigens and haptens of strategic, commercial, and medical importance such as bacterial capsular polysaccharides, the tricothecene T2, and bacterial lipid A. The stimulated production of antibodies is nonexistant or so low that attempted isolation of the antibody from serum would be impractical because of the large volume of serum needed to obtain a usable quantity of antibody. Similarly, production of the antibody is sometimes so slow that it may take several weeks or months to obtain any useful quantity of the antibody. A method that can induce formation of antibodies which can combat these and other haptens is, therefore, needed.

SUMMARY OF THE INVENTION

It is, therefore, an object of the present invention to provide a method for rapidly and efficiently producing large quantities of antibodies that are specific for selected antigens.

It is another object of this invention to provide a method for rapidly and efficiently producing large quantities of antibodies that are specific for weak antigens or haptens.

These and other objects are achieved by injecting IgD molecules from a first vertebrate species into a second vertebrate species, isolating the antibodies produced to the IgD molecules, conjugating antigens to immunoglobulins from the same animal species and of the same immunoglobulin class (isotype) as the anti-IgD antibody, injecting the anti-IgD antibody plus antigen-immunoglobulin conjugate into the first vertebrate species, and isolating the antibodies produced that are specific for the conjugated antigen.

In the preferred embodiment, IgD from a mouse is injected into a goat and the IgG antibody to the IgD is isolated. A hapten is bound to the isolated IgG and the IgG-hapten conjugate is injected into the mouse. The mouse generates large amounts of antibody specific for the IgG-hapten and, therefore, specific for the hapten.

Other objects, advantages, and novel features of the present invention will become apparent from the following detailed description of the invention.

DETAILED DESCRIPTION OF THE INVENTION

In the method described herein, antibodies to IgD are first produced by injecting IgD from a first vertebrate species (e.g., the mouse) with an adjuvant (e.g., complete Freund's adjuvant) into a second vertebrate species (e.g., the goat). IgG antibody specific for IgD of the first species can then be purified from serum obtained by bleeding the second species. When this purified anti-IgD antibody (e.g., goat anti-mouse IgD antibody) is injected into the first species (e.g., the mouse) the first species generates a large and rapid IgG response to the immunoglobulin (Ig) of the second species (i.e., mouse IgG anti-goat Ig). If a hapten or weak antigen, here designated as Al, is bound by chemical or other means to the anti-IgD antibody and the Al-anti-IgD antibody complex is injected into the first species, the first species generates a large and rapid IgG anti-Al antibody response along with a large and rapid IgG antibody response to the Ig of the second species. Most importantly, if Al is conjugated to normal Ig (i.e., normal goat IgG) that lacks anti-IgD specificity, from the second species, and is injected into the first species along with anti-IgD of the second species (e.g., goat IgG anti-mouse IgD) a large and rapid IgG anti-Al response will ensue, provided that the anti-IgD antibody and the normal Ig of the second species are of the same Ig class.

Any immunocompetent vertebrates can function in the invention but goats, rats, mice, rabbits, and humans are preferred, goats and mice being most preferred.

The anti-IgD antibody can be any of the five classes of immunoglobulins, IgA, IgD, IgE, IgG, and IgM, but IgG is the most preferred. Al can be any weak antigen or hapten, but haptens such as bacterial capsular polysaccharides, tricothecene T2, and bacterial lipid A are preferred, tricothecene T2 being most preferred. The antibodies produced by the first species after injection of the anti-IgD antibody can be any of the five classes of immunoglobulins, but IgG is produced in the largest quantities and is, therefore, most preferred.

Antibodies specific for Al can be isolated and used for any purpose suitable for antibody use. Particularly these antibodies are useful for detecting and quantifying Al, for purifying antigens Al by affinity chromatographic techniques, and for characterizing antigens Al. The antibodies specific for Al are particularly useful for protecting the vertebrate making anti-Al antibody or other vertebrates into which the antibodies are injected from a toxic Al.

In the preferred embodiment of this invention normal goat IgG (GIgG) was bound by chemical methods to a weak antigen or hapten. The resulting hapten-GIgG complex was injected along with purified anti-mouse IgD goat antibody (GaMIgD) into a mouse which produced large quantities of antibodies to the bound hapten molecule as well as to the goat IgG antibody. The antibodies, thus produced were isolated and used as described in the following examples.

The invention having been generally described, the following examples are given as particular embodiments of the invention and to demonstrate the practice and advantages thereof. It is understood that the examples are given by way of illustration and are not intended to limit the specification or the claims to follow in any manner.

The following abbreviations are used in the tables that display experimental data:

| Abbreviation | Explanation |
|---|---|
| FITC | Fluorescein isothiocyanate |
| FITC:GIgG Ratio | Molar ratio of FITC:GIgG in FITC-GIgG Conjugates |
| GIgG | Goat IgG |
| GaMIgD | Affinity purified goat anti-mouse IgD antibody |
| MSA | Mouse serum albumin |
| RIgG | Rabbit IgG |
| RaMIgD | Affinity purified rabbit anti-mouse IgD antibody |
| SRBC | Sheep red blood cells |
| SRBC-RaSRBC | A complex of SRBC and a rabbit anti-SRBC antibody |
| ug | Microgram |
| * | less than |

Antibody titers in all experiments are expressed as geometric means and standard errors (in parentheses) of values obtained by ELISA (enzyme linked immunosorbant assay). Each group was composed of 5 BALB/c mice. Titers can be used only to compare antibody responses of groups within a single experiment; not to compare responses of groups within different experiments.

In all of the experiments described herein, Al was bound to goat IgG by standard procedures. For example, FITC was bound to goat IgG by mixing FITC-celite with goat IgG at a 1:10 weight/weight ratio in 0.15 F NaCl/0.1 F NaHCO$_3$, pH 9.6 for 2 hours at room temperature. Celite was removed by centrifugation; free fluorescein was separated from FITC-goat IgG by gel filtration.

Examples I and II establish that mice injected with a hapten (FITC) bound to GIgG make a large anti-FITC antibody response if GaMIgD is injected along with the FITC-GIgG, but not if FITC-GIgG is injected in the absence of GaMIgD, and that the combination of FITC-GIgG and GaMIgD is as effective at inducing an anti-FITC antibody response as FITC bound directly to GaMIgD antibody.

| EXAMPLE I | | |
|---|---|---|
| Group | Antigens Injected | IgG1 anti-FITC Titer |
| A | 400 ug FITC-GIgG + 400 ug GIgG | *10 |
| B | 400 ug FITC-GIgG + 400 ug GaMIgD | 562. (1.18) |
| C | 400 ug GIgG + 400 ug FITC-GaMIgD | 392. (1.17) |

| EXAMPLE II | | |
|---|---|---|
| Group | Antigens Injected | IgG1 anti-FITC Titer |
| A | 400 ug FITC-GIgG + 400 ug GIgG | *10 |
| B | 400 ug FITC-GIgG + 400 ug GaMIgD | 747. (1.17) |
| C | 400 ug GIgG + 400 ug FITC-GaMIgD | 520. (1.09) |

Examples III and IV establish the optimal doses of FITC-GIgG and GaMIgD antibody for the generation of an anti-FITC antibody response:

| EXAMPLE III | | |
|---|---|---|
| Group | Antigens Injected | IgG1 anti-FITC Titer |
| A | 200 ug GaMIgD | *10 |
| B | 200 ug GaMIgD + 100 ug FITC-GIgG | 155. (1.22) |
| C | 200 ug GaMIgD + 200 ug FITC-GIgG | 900. (1.13) |
| D | 200 ug GaMIgD + 400 ug FITC-GIgG | 2,800. (1.21) |
| E | 200 ug GaMIgD + 800 ug FITC-GIgG | 4,600. (1.33) |
| F | 200 ug GaMIgD + 1600 ug FITC-GigG | 6,270. (1.09) |

| EXAMPLE IV | | | | |
|---|---|---|---|---|
| Group | GaMIgD | GIgD | FITC-GIgG | IgG1 anti-FITC Titer |
| A | 0 | 800 ug | 200 ug | 144. (1.36) |

EXAMPLE IV -continued

| Group | GaMIgD | GIgD | FITC-GIgG | IgG1 anti-FITC Titer |
|---|---|---|---|---|
| B | 12.5 ug | 788 ug | 200 ug | 146. (1.17) |
| C | 50. ug | 750 ug | 200 ug | 320. (1.35) |
| D | 100 ug | 700 ug | 200 ug | 1610. (1.38) |
| E | 200 ug | 600 ug | 200 ug | 3110. (1.14) |
| F | 400 ug | 400 ug | 200 ug | 6040. (1.48) |
| G | 800 ug | 0 | 200 ug | 3410. (1.10) |

Examples V and VI establish that the largest anti-FITC antibody responses are made in the presence of GaMIgD antibody when FITC-GIgG conjugates that have a molar conjugation ratio between 1 and 5 are used as antigen.

EXAMPLE V

| Group | Antigens Injected | FITC:GIgG RATIO | IgG1 Anti-FITC Titer |
|---|---|---|---|
| A | 200 ug GaMIgD + 400 ug FITC-GIgG | 0.5 | 2600. (1.05) |
| B | 200 ug GaMIgD + 400 ug FITC-GIgG | 1.8 | 29800. (1.18) |
| C | 200 ug GaMIgD + 400 ug FITC-GIgG | 5.7 | 10600. (1.13) |
| D | 200 ug GaMIgD + 400 ug FITC-GIgG | 17. | 59. (1.10) |
| E | 200 ug GaMIgD + 400 ug FITC-GIgG | 37 | 207. (1.21) |

EXAMPLE VI

| Group | Antigens Injected | FITC:GIgG RATIO | IgG1 Anti-FITC Titer |
|---|---|---|---|
| A | 200 ug GaMIgD + 400 ug FITC-GIgG | 0.5 | 1740. (1.14) |
| B | 200 ug GaMIgD + 400 ug FITC-GIgG | 1.3 | 8860. (1.43) |
| C | 200 ug GaMIgD + 400 ug FITC-GIgG | 2.1 | 7790. (1.47) |
| D | 200 ug GaMIgD + 400 ug FITC-GIgG | 4.6 | 6040. (1.20) |
| E | 200 ug GaMIgD + 400 ug FITC-GIgG | 6.5 | 3830. (1.43) |

Examples VII, VIII, IX, and X establish that when injected along with GaMIgD antibody, FITC must be bound to GIgG rather than to other immunogenic carrier molecules in order to generate a maximal anti-FITC antibody response.

EXAMPLE VII

| Group | Antigens Injected | IgG1 Anti-FITC Titer |
|---|---|---|
| A | 200 ug GaMIgD + 400 ug GIgG | *10 |
| B | 200 ug GaMIgD + 300 ug GIgG + 100 ug FITC-GIgG | 29300. (1.26) |
| C | 500 ug GIgG + 100 ug FITC-GIgG | *10 |
| D | 200 ug GaMIgD + 400 ug GIgG + 100 ug FITC-MSA | 125. (148) |
| E | 400 ug GIgG + 100 ug FITC-MSA | *10 |

EXAMPLE VIII

| Group | Antigens Injected | IgG1 Anti-FITC Titer |
|---|---|---|
| A | 200 ug GIgG + 400 ug FITC-GIgG | *10 |

EXAMPLE VIII -continued

| Group | Antigens Injected | IgG1 Anti-FITC Titer |
|---|---|---|
| B | 200 ug GaMIgD + 400 ug FITC-GIgG | 316000. (1.19) |
| C | 200 ug GIgG + 400 ug FITC-Ferritin | *10 |
| D | 200 ug GaMIgD + 400 ug FITC-Ferritin | 137. (1.29) |

EXAMPLE IX

| Group | Antigens Injected | IgG1 Anti-FITC Titer |
|---|---|---|
| A | 200 ug GIgG + 200 ug FITC-GIgG | *10 |
| B | 200 ug GaMIgD + 200 ug FITC-GIgG | 1430. (1.31) |
| C | 200 ug GIgG + 0.2 ml 10% FITC-SRBC | 23.7 (1.63) |
| D | 200 ug GaMIgD + 0.2 ml 10% FITC-SRBC | 84.4 (1.21) |
| E | 200 ug GIgG + 100 ug FITC-Ficoll | 60.6 (1.11) |
| F | 200 ug GaMIgD + 100 ug FITC-Ficoll | 175. (1.21) |
| G | 200 ug GIgG + 200 ug FITC-Avidin | *10 |
| H | 200 ug GaMIgD + 200 ug FITC-Avidin | *10 |

EXAMPLE X

| Group | Antigens Injected | IgG1 Anti-FITC Titer |
|---|---|---|
| A | 200 ug GIgG + 200 ug FITC-GIgG | *10 |
| B | 200 ug GaMIgD + 200 ug FITC-GIgG | 724. (1.14) |
| C | 200 ug GIgG + 200 ug FITC-KLH | 19.2 (1.37) |
| D | 200 ug GaMIgD + 200 ug FITC-KLH | 27.9 (1.56) |

Examples XI and XII establish that A1 must be bound to GIgG if injected along with GaMIgD or to RIgG when injected along with RaMIgD antibody to generate a maximal anti-A1 antibody response (i.e., the anti-IgD antibody and the carrier molecule to which A1 is bound must share antigenic determinants).

EXAMPLE XI

| Group | Antigens Injected | IgG1 Anti-SRBC Titer |
|---|---|---|
| A | 200 ug GIgG + 200 ug FITC-GIgG | *10. |
| B | 200 ug GaMIgD + 200 ug FITC-GIgG | 1,436. (1.31) |
| C | 200 ug GIgG + 200 ug FITC-RIgG | 46. (2.19) |
| D | 200 ug GaMIgD + 200 ug FITC-RIgG | 323. (1.28) |

EXAMPLE XII

| Group | Antigens Injected | IgG1 Anti-FITC Titer |
|---|---|---|
| A | 200 ug RIgG + 200 ug FITC-RIgG | *10. |
| B | 200 ug RaMIgD + 200 ug FITC-RIgG | 267. (1.31) |
| C | 200 ug RIgG + 200 ug FITC-GIgG | *10 |
| D | 200 ug FITC-RaMIgD + 200 ug FITC-GIgG | 107. (1.29) |

An experiment, Example XIII, was also performed that indicated that the anti-IgD antibody system could be used to generate antibodies to poorly immunogenic haptens that are conjugated to GIgG. The tricothecene mycotoxin T2 was bound to GIgG and injected into mice along with GaMIgD antibody. Serum antibody levels to T2 were titered 10 days later and were found to be 200-fold greater than those seen in mice injected with T2-GIgG in the absence of GaMIgD antibody or with GaMIgD antibody plus T2 that had been conjugated to an immunogenic carrier molecule other than GIgG (keyhole limpet hemocyanin).

EXAMPLE XIII

| Group | Antigens Injected | IgGl Anti-T2 Titer |
|---|---|---|
| A | 200 ug GaMIgD | *10. |
| B | 200 ug T2-GIgG | 34. +/− 7. |
| C | 200 ug GaMIgD + 200 ug T2-GIgG | 56,000. +/− 11,500. |
| D | 200 ug GaMIgD + 200 ug T2-KLH | 19. +/− 10. |

An additional experiment, Example XIV, indicated that the anti-IgD antibody system can be used to enhance antibody responses to complex antigens, such as SRBC, by binding the antigen involved to an immunoglobulin molecule (in this case, rabbit anti-SRBC antibody) and injecting it into mice with an anti-IgD antibody of the same species and isotype as the immunoglobulin in the immunoglobulin-antigen complex (RaMIgD).

EXAMPLE XIV

| Group | Antigens Injected | IgGl Anti-SRBC Titer |
|---|---|---|
| A | 200 ug RIgG + 0.2 ml 10% SRBC | 749. (1.13) |
| B | 200 ug RaMIgD + 0.2 ml 10% SRBC | 1530. (1.57) |
| C | 200 ug RIgG + 0.2 ml 10% SRBC-RaSRBC | 3800. (1.19) |
| D | 200 ug RaMIgD + 0.2 ml 10% SRBC-RaSRBC | 16100. (1.13) |

Two important points will not be evident from the data that is included. First, the great majority of the antibody produced in mice immunized with the anti-IgD system if of the IgGl isotype. Second, specific antibody is produced very rapidly in this system; in all of the experiments shown sera were obtained 7 to 10 days after immunization.

Obviously many modifications and variations of the present invention are possible in light of the above teachings. It is therefore to be understood that within the scope of the appended claims the invention may be practiced otherwise than as specifically described. The term "hapten" will be used within the claims to describe the weak antigens and haptens Al refered to in the specification.

What is claimed and desired to be secured by Letters Patent of the United States is:

1. A method for preparing antibodies to antigens comprising the steps of:
   injecting IgD immunoglobulins from a member of a first vertebrate species and an adjuvant into a member of a second vertebrate species, thereby producing anti-IgD antibodies in said member of said second vertebrate species;
   isolating said anti-IgD antibodies;
   obtaining non-specific immunoglobulins that are from the same vertebrate species and of the same isotypes as said anti-IgD antibodies;
   binding said nonspecific immunoglobulins to said antigens to form immunoglobulin-antigen conjugates;
   admixing said immunoglobulin-antigen conjugates with said anti-IgD antibodies to form a conjugate-antibody mixture;
   injecting said conjugate-antibody mixture into a member of said first vertebrate species, thereby producing anti-antigen antibodies that are specific to said antigens bounded to said non-specific immunoglo-bulins; and
   isolating said anti-antigen antibodies.

2. The method of claim 1 wherein said first and second vertebrate species are selected from the group consisting of goats, rats, mice, rabbits, and humans.

3. The method of claim 2 wherein said antibodies from said first and second veterbrate species are selected from the group consisting of IgA, IgD, IgE, IgG, and IgM antibodies.

4. The method of claim 3 wherein said antibodies from said first and second veterbrate species are IgG antibodies.

5. A method for preparing antibodies to haptens comprising the steps of:
   injecting IgD immunoglobulins from a member of a first vertebrate species and an adjuvant into a member of a second vertebrate species, thereby producing anti-IgD antibodies in said member of said second vertebrate species;
   isolating said anti-IgD antibodies;
   obtaining nonspecific immunoglobulins that are from the same vertebrate species and of the same isotypes as said anti-IgD antibodies;
   binding said nonspecific immunoglobulins to haptens to form immunoglobulin-hapten conjugates;
   admixing said immunoglobulins-hapten conjugates with said anti-IgD antibodies to form a conjugate-antibody mixture;
   injecting said conjugate-antibody mixture into a member of said first vertebrate species, thereby producing anti-hapten antibodies that are specific for said haptens that were bound to said nonspecific immunoglobulins; and
   isolating said anti-hapten antibodies.

6. The method of claim 5 wherein said first and second vertebrate species are selected from the group consisting of goats, rats, mice, rabbits, and humans.

7. The method of claim 6 wherein said antibodies from said first and second vertebrate species are selected from the group consisting of IgA, IgD, IgE, IgG, and IgM antibodies.

8. The method of claim 7 wherein said antibodies from said first and second vertebrate species are IgG antibodies.

9. The method of claim 8 wherein said hapten in said immunoglobulin-hapten conjugates is selected from the group consisting of bacterial capsular polysaccharides, tricothecene T2, and bacterial lipid A.

10. The method of claim 9 wherein said hapten in said immunoglobulin-hapten conjugates is tricothecene T2.

11. A method for preparing antibodies to haptens comprising the steps of:
   injecting IgD immunoglobulins from a member of a first vertebrate species and an adjuvant into a member of a second vertebrate species, thereby producing anti-IgD antibodies in said member of said second vertebrate species;
   isolating said anti-IgD antibodies;
   binding said anti-IgD antibodies to haptens to form anti-IgD antibody-hapten conjugates;
   injecting said anti-IgD-hapten conjugates into said first vertebrate species, thereby producing anti-haptens antibodies that are specific to said haptens; and
   isolating anti-hapten antibodies.

12. The method of claim 11 wherein said first and second vertebrate species are selected from the group consisting of goats, rats, mice, rabbits, and humans.

13. The method of claim 12 wherein said hapten in said anti-IgD antibody hapten conjugates is selected from the group consisting of bacterial capsular polysaccharides, tricothecene T2, and bacterial lipid A.

14. The method of claim 13 wherein said hapten in said anti-IgD antibody hapten conjugates is tricothecene T2.

15. The method of claim 13 wherein said first and second vertebrate species are selected from the group consisting of goats, rats, mice, rabbits, and humans and said antibodies from said first and second vertebrate species are IgG antibodies.

16. The method of claim 14 wherein said first and second vertebrate species are selected from the group consisting of goats, rats, mice, rabbits, and humans and said antibodies from said first and second vertebrate species are IgG antibodies.

* * * * *